(12) United States Patent
Joshi

(10) Patent No.: US 6,591,133 B1
(45) Date of Patent: Jul. 8, 2003

(54) APPARATUS AND METHODS FOR FLUID DELIVERY USING ELECTROACTIVE NEEDLES AND IMPLANTABLE ELECTROCHEMICAL DELIVERY DEVICES

(75) Inventor: Ashok V. Joshi, Salt Lake City, UT (US)

(73) Assignee: Microlin LLC, Salt Lake City, UT (US)

( * ) Notice: Subject to any disclaimer, the term of this patent is extended or adjusted under 35 U.S.C. 154(b) by 54 days.

(21) Appl. No.: 09/723,230

(22) Filed: Nov. 27, 2000

(51) Int. Cl.$^7$ ................................................. A61N 1/30

(52) U.S. Cl. ............................ 604/21; 604/30; 604/36; 604/289

(58) Field of Search .......................... 604/890.1, 891.1, 604/892.1, 19–21, 27, 30, 36, 289

(56) References Cited

U.S. PATENT DOCUMENTS

| | | | |
|---|---|---|---|
| 3,964,482 A | * 6/1976 | Gerstel et al. ............... 424/449 |
| 4,003,379 A | 1/1977 | Ellinwood, Jr. |
| 4,127,708 A | * 11/1978 | Liang et al. ............... 429/218.1 |
| 4,141,359 A | 2/1979 | Jacobsen et al. |
| 4,258,109 A | * 3/1981 | Liang et al. ............... 429/218.1 |
| 4,263,377 A | * 4/1981 | Joshi et al. ............... 429/231.5 |
| 4,317,874 A | * 3/1982 | Joshi et al. ............... 429/213 |
| 4,377,624 A | * 3/1983 | Joshi et al. ............... 429/320 |
| 4,452,249 A | 6/1984 | Sachs et al. |
| 4,978,337 A | * 12/1990 | Theeuwes ............... 604/251 |
| 5,035,711 A | 7/1991 | Aoki et al. |
| 5,041,107 A | 8/1991 | Heil, Jr. |
| 5,063,175 A | 11/1991 | Broadbent |
| 5,250,023 A | 10/1993 | Lee et al. |
| 5,286,254 A | 2/1994 | Shapland et al. |
| 5,538,605 A | * 7/1996 | Joshi et al. ............... 204/266 |
| 5,593,552 A | * 1/1997 | Joshi et al. ............... 204/230.5 |
| 5,622,530 A | * 4/1997 | Phipps ............... 604/20 |
| 5,647,844 A | * 7/1997 | Haak et al. ............... 424/449 |
| 5,700,481 A | 12/1997 | Iga et al. |
| 5,871,460 A | * 2/1999 | Phipps et al. ............... 604/20 |
| 5,911,223 A | 6/1999 | Weaver et al. |
| 5,961,483 A | * 10/1999 | Sage et al. ............... 424/449 |
| 5,978,701 A | * 11/1999 | Johnson et al. ............... 235/449 |
| 5,985,316 A | * 11/1999 | Gyory et al. ............... 424/449 |
| 5,993,435 A | * 11/1999 | Haak et al. ............... 604/20 |
| 6,001,088 A | 12/1999 | Roberts et al. |

(List continued on next page.)

FOREIGN PATENT DOCUMENTS

WO    WO 96/16693    * 6/1996    ............ A61N/1/30

OTHER PUBLICATIONS

PCT International Search Report, PCT/US01/45421, date Jun. 14, 2002, 3 pages.

Primary Examiner—Ira S. Lazarus
Assistant Examiner—Andrea M. Ragonese
(74) Attorney, Agent, or Firm—TraskBritt

(57) ABSTRACT

The invention includes apparatus and methods for electrotransport of a drug or other beneficial agent through a skin or mucosal membrane surface. In one embodiment, at least one of the cathode or anode electrode of an electrochemical cell is configured, at least in part, as an electroactive needle for insertion all or part way through the stratum corneum of a patient's skin. A reservoir containing a beneficial agent may be provided in fluid communication with one or more electroactive needles, in which case the electroactive needle (s) may be configured with a hollow bore interior for transport of the beneficial agent directly into a subject's tissues. In a related embodiment, an electroactive needle is configured for intravenous and/or intramuscular use. The invention also includes an electrotransport system comprising an electrochemically active porous substrate. In a further embodiment, the invention comprises an electrotransport system having one or more implantable active porous electrodes.

30 Claims, 8 Drawing Sheets

U.S. PATENT DOCUMENTS

| | | | | |
|---|---|---|---|---|
| 6,041,252 A | * | 3/2000 | Walker et al. | 435/173.6 |
| 6,060,196 A | * | 5/2000 | Gordon et al. | 204/283 |
| 6,060,197 A | * | 5/2000 | McEvoy et al. | 429/166 |
| 6,071,508 A | * | 6/2000 | Murdock | 424/449 |
| 6,086,572 A | * | 7/2000 | Johnson et al. | 604/20 |
| 6,219,574 B1 | * | 4/2001 | Cormier et al. | 600/362 |
| 6,230,051 B1 | * | 5/2001 | Cormier et al. | 600/573 |
| 6,256,533 B1 | | 7/2001 | Yuzhakov et al. | |
| 6,298,254 B2 | * | 10/2001 | Tamada | 600/347 |
| 6,328,728 B1 | * | 12/2001 | Holladay et al. | 604/501 |
| 6,355,025 B1 | * | 3/2002 | Phipps et al. | 604/20 |
| 6,379,324 B1 | * | 4/2002 | Gartstein et al. | 604/20 |
| 2002/0016562 A1 | * | 2/2002 | Cormier et al. | 604/20 |

\* cited by examiner

APPARATUS AND METHODS FOR FLUID DELIVERY USING ELECTROACTIVE NEEDLES AND IMPLANTABLE ELECTROCHEMICAL DELIVERY DEVICES

TECHNICAL FIELD

The present invention relates to apparatus and methods for delivering drugs and other beneficial agents. More specifically, the present invention relates to apparatus and methods for subcutaneous, transdermal, intravenous, and intramuscular delivery of drugs and other beneficial agents to a subject.

BACKGROUND

In an effort to improve the convenience of drug delivery, provide accurate dosing, and improve efficacy, various invasive and non-invasive drug delivery systems have been devised. The many techniques for delivering drugs include direct injection into body tissues, oral administration, intravenous administration, and transdermal delivery through the skin. As used herein, transdermal delivery means introduction of drugs or other beneficial agents through, or by way of, the skin. Except in the case of transdermal delivery, the above-mentioned drug delivery systems typically provide for systemic administration of drugs in that the drug is delivered throughout the body by the bloodstream. In the case of transdermal delivery, passive diffusion and active transport mechanisms can be used for more localized delivery of drugs into the tissues.

Each type of drug delivery system has its own advantages over the various other delivery technologies. Most recently, transdermal drug delivery has been shown to offer particular promise for a number of reasons. As an alternative to medicines administered orally, transdermal drug delivery avoids the "first-pass" metabolism of the liver, allowing for relatively lower doses and more controlled delivery of conventional forms of certain drugs. In contrast to the direct injection of drugs, transdermal drug delivery allows for continuous and convenient drug administration over an extended time period. Transdermal delivery techniques can, in some applications, allow a subject unrestricted mobility, a benefit not afforded by many intravenous drug administration systems.

The low permeability of the outer surface of mammalian (including human) skin, however, provides a formidable barrier to the transdermal administration of drugs at therapeutic levels. The skin's outermost layer, the epidermis, acts as the primary resistive barrier to drug diffusion. The epidermis can be most basically described as an avascular layer of stratified squamous keratinised epithelium sitting on a basement membrane. The epithelium can be sub-divided into four primary layers from the base to the free surface. The most resistive layer of the epidermis forms a superficial water-resistant protective layer called the stratum corneum. The stratum corneum is composed of layers of dead tissue, essentially consisting of flattened cells filled with cross-linked keratin together with an extracellular matrix made up of lipids arranged largely in bilayers. Underlying the stratum corneum are the further layers of the epidermis, generally comprising three layers commonly identified as the stratum granulosum, stratum spinosum, and stratum basale. These further layers of the epidermis are followed by the dermis, which contains two layers, the papillary dermis and the reticular dermis.

One class of techniques for overcoming the resistive barriers imposed by intact skin is assisted diffusion of a drug through the epidermis by "electrotransport" processes. Using the principles of electrotransport, a direct electrical current or an electrical potential gradient is used to actively transport the drug transcutaneously into the body. The composition of the stratum corneum, however, is such that its innate resistance to the flow of electrons is relatively high in comparison to other underlying body tissue (e.g., the further layers of the epidermis and the blood vessels therein).

Electrotransport processes are presently used in a wide variety of therapeutic drug delivery applications. One method of using electrotransport for transdermal drug delivery is known as "iontophoresis." In iontophoresis, the diffusion of an ionized drug (e.g., salts of a pharmaceutical or other drug which, when dissolved, form charged ions) across the stratum corneum and into the dermal layers a skin surface is enhanced by the direct application of a mild electrical potential to the skin. Typically, the permeation rate (or "flux") of the ionized drug compound will be directly proportional to the strength of the applied electric current. A second type of electrotransport process called "electroosmosis," involving the transdermal flux of a liquid solvent containing an uncharged drug or pharmaceutical agent, has been recognized as a means for delivery of an uncharged drug or agent into the body. Electroosmosis, in which the solvent convectively moves through a "charged pore" in response to the preferential passage of counter ions, can be induced by the presence of an electric field imposed across the skin by the active electrode of an iontophoretic device. A third type of electrotransport is known as "electroporation." Electroporation can be used for drug or other agent transport by altering lipid bilayer permeability through the formation of transiently existing pores in the skin membranes.

At any given time during electrically assisted drug or agent delivery, more than one of these electrotransport processes may be occurring simultaneously to some extent.

As illustrated by FIG. 1, a typical iontophoretic system 16, similar to the iontophoretic system disclosed in U.S. Pat. No. 5,618,265 to Meyers et al., involves the placement of two oppositely charged "donor and counter" electrodes (an anode and a cathode) 18, 20 on a subject's skin surface 30 at or around a tissue region selected for therapeutic application. A reservoir 22 containing the ionized drug to be delivered is placed under the electrode bearing the same charge as the drug (the "donor electrode"). Thus, in anodal iontophoresis, as is shown in FIG. 1, a positively charged drug is placed under the positively charged anode electrode 18. Conversely, if the ionized drug to be delivered were negatively charged, then the negative electrode (cathode) 20 would be the active electrode under which the ionized drug would be placed. An ion-conducting adhesive 28 may be situated under each electrode 18, 20 for stabilization of the electrodes. Electrolytes are typically added-to the solution containing the ionized drug so that current can be easily conducted. A selectively permeable membrane (not shown) may further be placed under the active electrode 18 to allow for selective flow of particular types of charged and uncharged species into skin surface 30. A voltage source 24, typically a battery, supplies direct electric current by conductive wires 26 extending to the electrodes. At electrodes 18, 20, the current is converted to an ionic current by a series of oxidation-reduction reactions.

To activate the system, electrodes 18, 20 are spaced apart from one another on skin surface 30 where skin surface 30 acts as a conductor to complete the electrical circuit of iontophoretic system 16. Upon activation of iontophoretic system 16, the charged drug is repelled by active electrode 18 into the skin 30 (as indicated by the arrows), thereby initiating drug transport by electrostatic repulsion, ionic conduction, and other cooperating electrotransport processes.

Representative iontophoretic systems are disclosed in U.S. Pat. No. 5,618,265 to Myers et al. and U.S. Pat. Nos. 5,647,844 and 4,927,408 to Haak et al. Other patents discussing a variety of iontophoresis systems, iontophoresis electrodes, and/or methods of iontophoretically administering medicament ions include U.S. Pat. Nos. 4,744,787 to Phipps et al., U.S. Pat. No. 4,752,285 to Petelenz et al., U.S. Pat. No. 4,820,263 to Spevak et al., U.S. Pat. No. 4,886,489 to Jacobsen et al., U.S. Pat. No. 4,973,303 to Johnson et al., and U.S. Pat. No. 5,125,894 to Phipps et al.

Modern galvanic transdermal delivery systems have been disclosed in U.S. Pat. No. 5,618,265 to Myers et al. and U.S. Pat. Nos. 5,647,844 and U.S. Pat. No. 4,927,408 to Haak et al. Myers et al. and Haak et al. generally discuss forming the counter and donor electrodes of dissimilar metals or materials with different half cell reactions. The electrode materials discussed generally include a zinc anode and silver chloride cathode. The voltage generated by the zinc and silver chloride galvanic couples of the references is, however, only about 1 volt, a level insufficient to assist in the therapeutic transdermal delivery of many drugs and other beneficial agents.

Although other transport mechanisms such as electroporation and electroosmosis are involved in the movement of the charged drug through the skin, the efficacy of this process depends largely upon ionizable pharmaceuticals or other drugs. Compounds which are hydrophobic and/or which have a relatively high molecular weight (e.g., many peptide and protein drugs) are less susceptible to iontophoretic delivery. Additionally, the physiological pH of human skin is between 3 and 4, thus causing the surface of the skin to be negatively charged due to a preponderance of carboxylic acid functionalities of negatively charged amino acid residues. As a result of this net negative charge, the skin functions as a selective membrane in allowing the transport of positively charged drug species to proceed with less resistance than the transport of negatively charged drug species. (Burnette and Ongpipattanakul, 1987). Peptide and protein drugs are particularly affected by pH, which exerts a major influence on their isoelectric point. Thus, the characteristic charge associated with an ionizable drug in conjunction with the pH of the skin may render certain drugs more susceptible to iontophoretic transport than others. Also influencing the effectiveness of iontophoretic delivery are many complicating factors that vary with age, gender, race, site of iontophoretic delivery, and skin characteristics of particular individuals (e.g., skin quality, skin follicle density, etc.). The interface between an electrode and the skin can act as a further limiting factor such as when the surface contact of an electrode is poor, or when the skin tissue is dry and clean. Finally, the transdermal delivery of many drugs requires that the iontophoretic apparatus be configured to achieve a "skin breakthrough voltage" of a particular threshold to initially overcome the rigorous impedance barrier of the stratum corneum. Once the impedance barrier of the stratum corneum has been broken down by the "skin breakthrough voltage," a follow-on voltage of a much lesser intensity is capable of continuing the transdermal facilitation of the drug across the skin barrier. The need for a "skin breakthrough voltage" in the transdermal application of many drugs limits the usefulness of many prior art galvanic iontophoretic devices, which are typically configured as relatively low voltage systems.

Currently, there has been a renewed interest in the use of the various transdermal delivery systems, due mainly to the widespread acceptance of passive transdermal patches and recent breakthroughs in recombinant DNA technology leading to the discovery of a large number of therapeutically important peptides and proteins. Accordingly, a need exists for an improved electrotransport system that overcomes the resistive properties of the skin while overcoming many, if not all, of the aforementioned drug delivery problems associated with conventional iontophoretic techniques.

DISCLOSURE OF THE INVENTION

The invention includes apparatus and methods for electrically assisted transport ("electrotransport") of a drug or other beneficial agent through a skin or mucosal membrane surface, wherein at least one of the cathode or anode electrode of an electrochemical cell is configured, at least in part, as an electroactive needle adapted to be inserted all or part way through the stratum corneum of a subject's skin, resulting in direct current flowing from the electroactive needle through the tissues of the subject. As used herein, a "subject" will typically be a mammal.

The direct current generated by the apparatus of the present invention bypasses the cutaneous keratin layer of the skin, resulting in enhanced transdermal delivery of a drug or other beneficial agent into the tissues underlying and/or surrounding the electroactive needle(s). A reservoir containing a drug or other beneficial agent may be provided in fluid communication with one or more electroactive needles, in which case the electroactive needle(s) may be configured with a hollow bore interior extending therethrough for transport of the drug or other beneficial agent directly into a subject's tissues. The drug or other beneficial agent is preferably provided as a liquid or dissolved in a fluid or solvent such that it is otherwise in liquid form. In a related embodiment, the electroactive needle of the present invention may be configured of a length and shape suitable for intravenous and/or intramuscular delivery of a drug or other beneficial agent.

An apparatus of the present invention for transdermal, intradermal and/or subcutaneous delivery of a drug or other beneficial agent includes an electrochemical cell having an electrochemically active cathode and an electrochemically active anode wherein at least a portion of at least one of the cathode and anode is configured as at least one electroactive needle.

The present invention also includes a method of electrically facilitating the transport of a drug or other beneficial agent through body tissues of a subject. The method comprises providing an anode configured to conduct current in relation to a first skin surface, providing a cathode and an anode configured to conduct current in relation to a respective skin surfaces wherein at least a portion of at least one of the cathode and anode are configured as at least one electroactive needle of a predetermined length, providing at least one conductor extending between and electrically interconnecting the anode with said cathode, providing a drug or other beneficial agent reservoir disposed adjacent and in fluid communication with an electrically conducting area of at least one of the anode and the cathode, inserting the electroactive needle a predetermined distance into a skin surface to electrochemically activate the anode and cathode, electrochemically generating a voltage from the activation of the anode and the cathode, and delivering voltage to the body tissues of a subject to facilitate the transport of a drug other beneficial agent though the body tissues of the subject.

In a multi-needle embodiment of the present invention, the cathode and/or anode may be formed of a plurality of electroactive needles.

The electrotransport apparatus of the present invention may further include a battery, power cell, or one or more additional electrochemical cells, to boast the voltage of the apparatus. A resistor can be added to control the voltage flow. The device can be further configured to deliver medication contained in standard medication cartridges.

As a further embodiment, an implantable electrotransport system is disclosed wherein one of the anode or cathode of an electrochemical cell is implanted under a skin surface. In a preferred embodiment, the implantable electrode is configured as a porous or micro-porous metal substrate which allows drugs or other beneficial agents to flow therethrough. A battery and resistor may be provided to enhance the performance of the device.

The present invention also includes a porous or microporous metal substrate electrode, comprising either the anode or the cathode of an electrochemical cell, mounted on a skin surface for the electrically assisted delivery of drugs or other beneficial agents through the skin.

In a still further embodiment, an electrotransport system having active porous electrodes is disclosed wherein the electrotransport system is entirely implantable under a skin surface.

BRIEF DESCRIPTION OF THE SEVERAL VIEWS OF THE DRAWINGS

In the drawings, which illustrate what is currently considered to be the best mode for carrying out the invention.

BEST MODE OF THE INVENTION

Although it has broader utility, the present invention may best be described in relation to the electrotransport of drugs or other beneficial agents across a skin or mucosal membrane surface of a mammalian subject.

Figure 1:
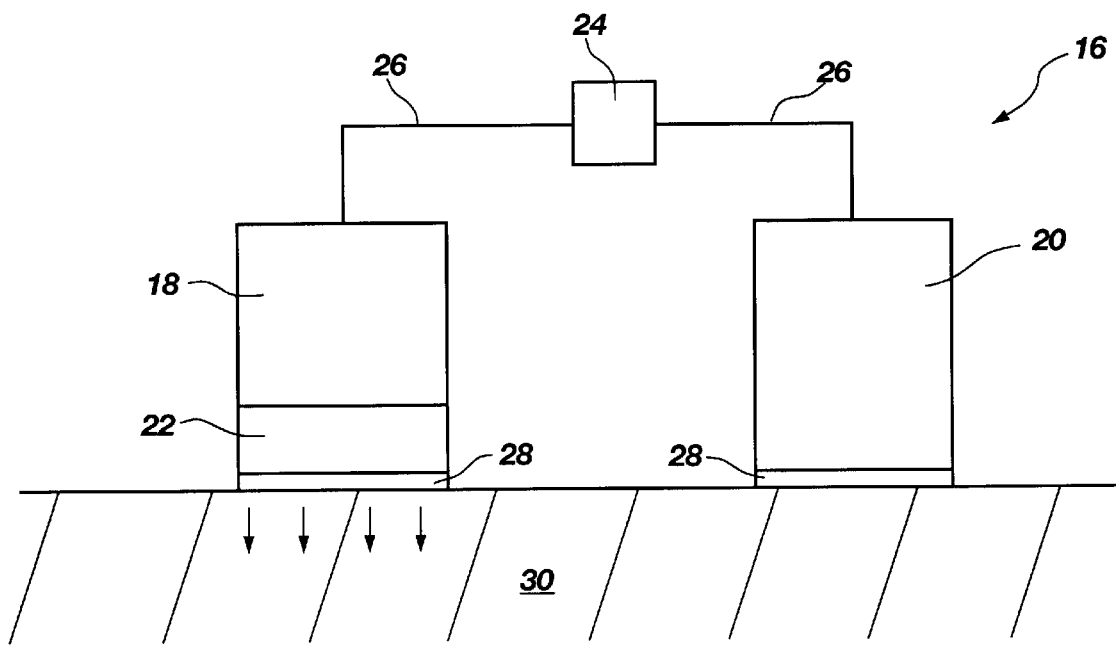
FIG. 1 is a schematic representation of an exemplary prior art transdermal drug delivery device.
Figure 2:
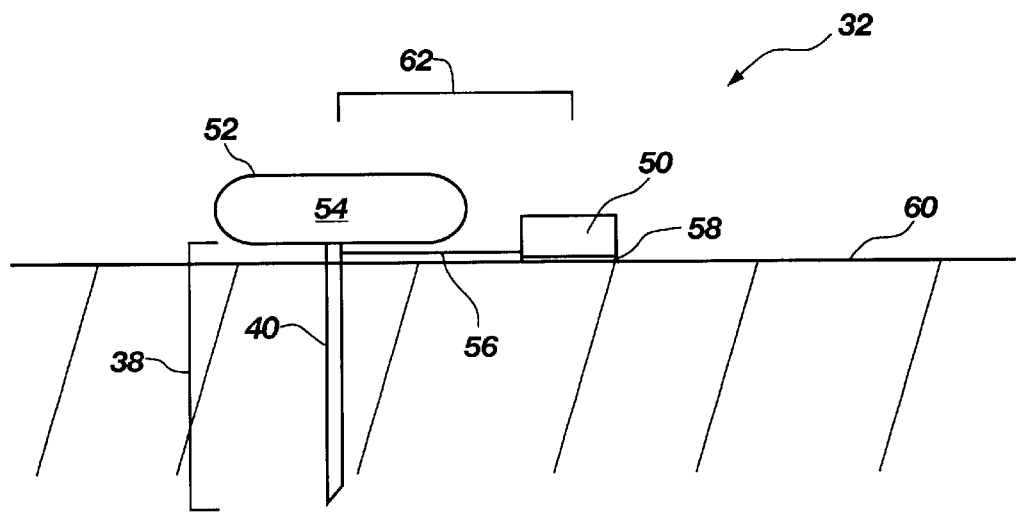
FIG. 2 is a schematic view of a preferred embodiment of an electrochemical transdermal delivery system according to the present invention.

In a preferred embodiment of the invention (FIG. 2), a galvanic and/or electrically powered electrotransport system 32 ("electrotransport system 32") for the transdermal, intradermal and/or subcutaneous delivery of drugs or other beneficial agents comprises an electrochemically powered system including at least two electrically interconnected electrochemically active electrodes 38, 50 of differing electrode potentials ("active and receiving" electrodes), wherein an "active" electrode 38 is configured, at least in part, as an electrochemically active ("electroactive") needle 40 to be inserted into a skin or mucosal membrane surface ("skin surface") 60. As shown in FIG. 2, substantially all of electrode 38 is formed as an electroactive needle 40. Electrodes 38, 50, and hence electroactive needle 40, comprise components of an electrochemical cell 62.

As used herein, the term "electrotransport" refers to the facilitated migration of beneficial fluids through body tissue in response to the flow of electrons. Electroosmosis, electroporation, iontophoresis, and combinations of any of these are thus contemplated by the use of the term "electrotransport." In the current context, however, such "electrotransport" generally occurs beneath the stratum corneum.

When inserted into a skin surface 60, electroactive needle 40 participates in the generation of electrical current, and then delivers that electrical current to underlying and/or surrounding tissues of a subject. In turn, the electrical current generated by electrochemical cell 62 facilitates the trandermal flux of drugs or other beneficial agents through selected body tissues of a subject.

Electroactive needle 40 will also preferably be formed with an internal passageway extending therethrough. As such, electroactive needle 40 can be used for direct delivery of drugs or other beneficial agents into body tissues underlying the skin's outer surface.

In FIG. 2, electroactive needle 40 is shown after insertion into a skin surface 60 of a patient. A "receiving" electrode 50 is placed on a skin surface 60 at a location which is spaced apart from an upper surface of inserted active electrode 38. Receiving electrode 50 is preferably constructed to be thin and flexible, and to conform to the surface of a patient's skin. Conductive wire 56 provides an electrical path between electrodes 38, 50, thus establishing an electrochemical cell 62. Preferably underlying receiving electrode 50 is a conductive adhesive 58 for stabilizing receiving electrode 50 on skin surface 60 while preserving the electrode's ability to conduct current in relation to skin surface 60. A polyacrylamide gel may be substituted for conductive adhesive 58.

A reservoir 52, normally containing a drug or other beneficial agent in liquid form ("beneficial fluids") 54, is positioned adjacent active electrode 38 such that the contents of reservoir 52 are in fluid communication with a hollow bore portion of electroactive needle 40. Use of the term "liquid" in the context of the drug or other beneficial agent should be understood to mean one or more drugs or beneficial agents provided in a fluid or solvent carrier or other form having a suitable rheology for gravity assisted and/or electrically assisted and/or pressure assisted flow through the bore of the electroactive needle of the present invention. The beneficial fluids 54 in reservoir 52 are preferably provided without an ionic charge to prevent electrostatic repulsion or attraction in relation to electroactive needle 40. As such, initially-charged beneficial agents comprising the beneficial fluids 54 may have their charge neutralized by various drug carriers known to those of skill in the art. As one example, drug carriers comprising cationic liposomes, dendrimers, and other polymers can be used to bind to oligonucleotides to neutralize their anionic charge.

Active electrode 38, to include the electroactive needle 40 portion thereof which may comprise all or part of active electrode 38, can be formed as either an anode or a cathode. When one of electrodes 38, 50 is formed as an anode, the electrode can be comprised of any active metal, but is preferably comprised, at least in part, of Zn, Mg, Ca, Ba, Al, Sn, Fe, including alloys and mixtures of any of these. The corresponding cathode electrode will then typically comprise any of the active metal oxides, halides, and chalcogenides, but will preferably comprise carbon, silver oxides, copper oxides, manganese dioxides, lithium, and mixtures thereof.

Figure 3:
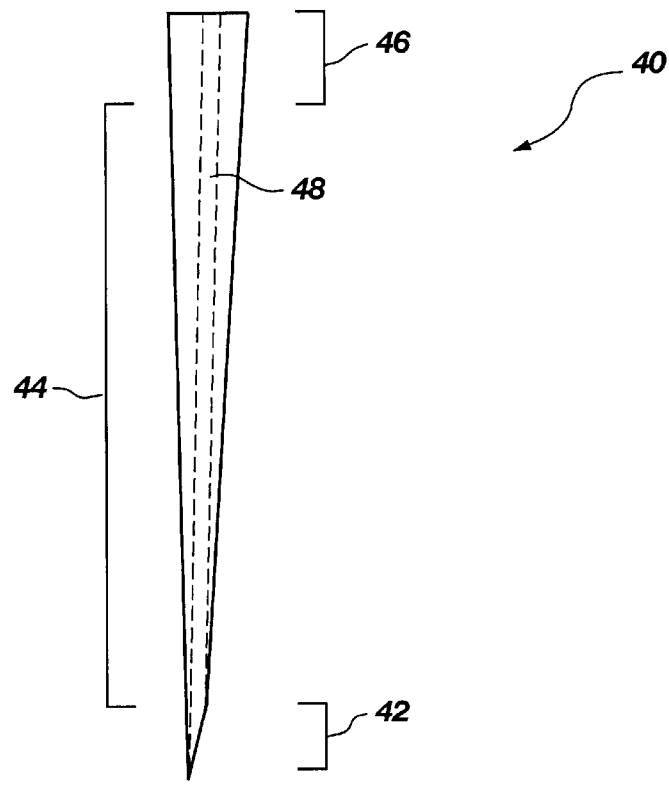
FIG. 3 is a cross-sectional representation of a preferred embodiment of an electroactive needle of the present invention.

As can be seen in FIG. 3, the electroactive needle 40 of active electrode 38 is constructed with a hollow bore interior or passageway 48 extending from external openings at both ends of electroactive needle 40 for voltage-enhanced delivery of beneficial fluids 54 through a skin surface 60 of a patient. Electroactive needle 40 is preferably tapered, and comprises a tip 42 for insertion into skin surface 60, a downwardly extending hollow shaft 44, and a shank end 46 which is positioned proximate skin surface 60 after insertion of electroactive needle 40 into skin 60.

With reference to FIGS. 2 and 3, shank end 46 is configured to be integrated with an air-tight fitting (not shown) of reservoir 52, the air-tight fitting such that the contents of reservoir 52 can flow through the external opening of shank 46 and into a hollow bore portion of electroactive needle 40 while being completely sealed at the interface of shank end 46 and reservoir 52. Thus, a fitting of reservoir 52 may comprise, for example, a connecting interface such as an O-ring configuration, or other sealable arrangement known to those of skill in the art. Alternatively, reservoir 52 may be fashioned such that a functional interface is accomplished by sealably molding or adhering a portion of reservoir 52 over an end portion of shank end 46. Shank end 46 may also be configured with suitable interface fittings known in the art, as well as a sharp projecting tab (not shown) for puncturing a fluid-retaining portion of reservoir 52 during the, installation of reservoir 52. When beneficial fluids 54 are placed in reservoir 52, the result of the interface of reservoir 52 with shank end 46 leads to the two components in fluid communication with one another.

Referring again to FIG. 3, tip 42 is normally configured to be open-ended such that a liquid may be delivered through the hollow bore interior of shank end 46 and shaft 44, and out of tip 42. Tip 42 may also be formed as a porous end or as otherwise having arranged multiple openings for various distribution patterns in the delivery of a beneficial fluid. Shaft 44 may also be configured as porous, in whole or in part. Shaft 44 extends to a predetermined length consistent with the desired therapeutic application. For example, shaft 44 will preferably extend through some, most, or all of the stratum corneum for delivery of beneficial fluids 54 to underlying and/or surrounding tissues. Preferably, shaft 44 will extend electroactive needle 40 to a length that is slightly longer than the depth of the stratum corneum. Typically, the length for shaft 44 in this embodiment will be 2 mm or less so that tip 42 will not bruise capillary vessels in the vascular papillary and reticular tissue layers of the dermis.

Figure 4:
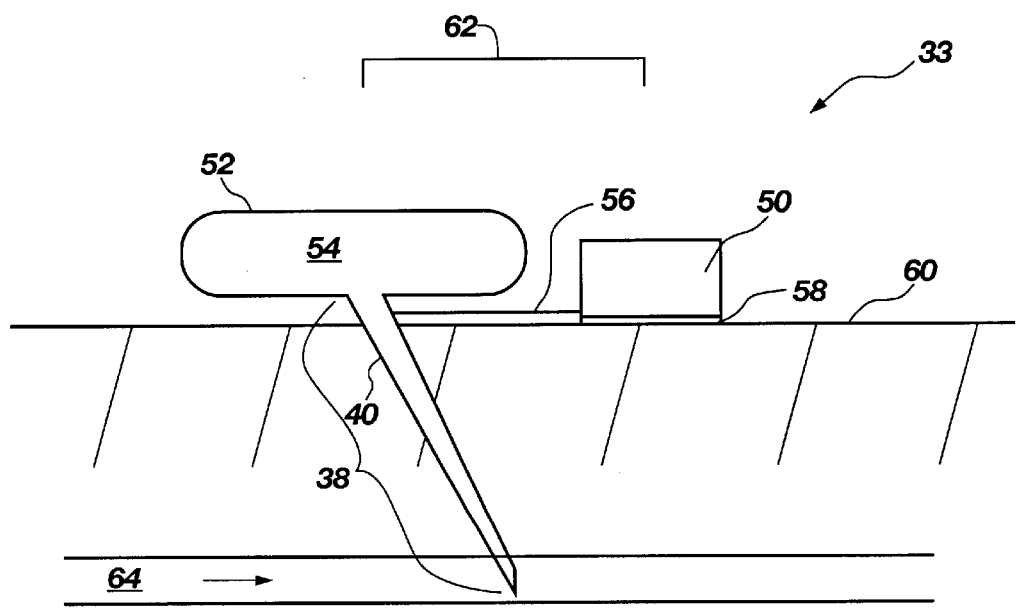
FIG. 4 illustrates an embodiment of the transdermal delivery system of the present invention for use in intravenous, subcutaneous, intramuscular or similar delivery of a drug or other beneficial agent.

Shaft 44 may also be configured of a length suitable for intravenous or intramuscular delivery of beneficial fluids 54. An example of an intravenous delivery embodiment of the present invention is shown in FIG. 4.

The diameter of shaft 44 may vary substantially, dependent upon the particular application used. In most applications, shaft 44 will be configured to be narrow enough such that the insertion of shaft 44 into the skin results in little or no bruising or swelling of the skin, while still permitting the voltage-enhanced delivery of beneficial fluids through the hollow passageway of shaft 44 and tip 42. Typically, shaft diameters of up to 400 $\mu$m are preferred to limit damage to skin 60. Shaft 44 may also be formed of various larger diameters or irregular diameters, and with larger or varying hollow interiors therein to increase or alter the flow of beneficial fluids. In another preferred embodiment, at least a portion of shaft 44 may be electrically insulated from the skin for more focused delivery of electrochemically generated voltage, preferably with a biocompatible insulator. For example, various non-toxic polymeric resins (e.g., silicone rubber), ceramic materials or blends thereof (e.g, hydroxyapatite blends) may be used for insulating shaft 44.

Shaft 44 may be alternatively coated with a microporous and micro-thin (preferably on the order of microns) separator material known in the art, including materials comprising microporous polymers such as polypropylenes, polyethylenes, polytetrafluoroethenes (PFTEs), and the like, to enhance the mechanical and chemical surface properties shaft 44 by reducing friction, fretting, fatigue, and by providing corrosion resistance. Along with conventional coating processes such as spraying or dipping and vacuum deposition techniques, surface modification technologies as diffusion, laser and plasma processes, chemical plating, grafting or bonding, hydrogel encapsulation, and bombardment with high-energy particles may be used in the application of such coatings. Antimicrobial and antibacterial treatments and coatings known in the art may also be employed in addition to each of the coatings previously described. Antimicrobial and antibacterial treatments and coatings may also be applied directly to shaft 44.

Referring again to FIG. 2, insertion of electroactive needle 40 into skin surface 60, in conjunction with placement of receiving electrode 50 over a second skin or mucosal membrane surface, closes the electrical circuit between electrodes 38, 50, thus activating electrotransport system 32. The sub-stratum corneum tissue layer provides a portion of the electroconductive pathway of the electrochemical cell. Upon activation of electrotransport system 32, a voltage is generated by the electrochemical interaction of electrodes 38, 50, causing electrons to be released from anode electrode 38 and consumed at cathode electrode 50. Since electroactive needle 40 forms at least a portion of active electrode 38, electroactive needle 40 participates in the electrochemical generation of voltage in electrotransport system 32. A steady direct current is thus applied between electrodes 38, 50. The voltage generated by electrodes 38, 50 increases the rate of transdermal, intradermal and/or subcutaneous flux by reducing the physical resistance and/or enhancing the permeability of underlying and/or surrounding tissue layers. Thus, as current flows between electrodes 38, 50 placed at spaced apart locations under and on skin 60, the current path facilitates the movement of beneficial fluid 54 through the desired underlying and/or surrounding tissues of the patient, and in some instances, facilitates the movement of beneficial fluid 54 into the systemic circulation.

In an intravenous delivery embodiment 33 of the apparatus, illustrated in FIG. 4, shaft 44 extends downwardly through skin surface 60 to a predetermined distance such that tip 42 of electroactive needle 40 pierces and resides in a vein 64. When inserted through skin surface 60, shaft 44 and/or tip 42 will preferably be slanted or angled in relation to vein 64 such that the flow of blood within vein (as indicated by the arrow) will not substantially interfere with the flow of fluids from tip 42. The desired slant or angle of shaft 44 may arise from either a slanted design of shaft 44, or from the angle of insertion of electroactive needle 40.

Figure 5:
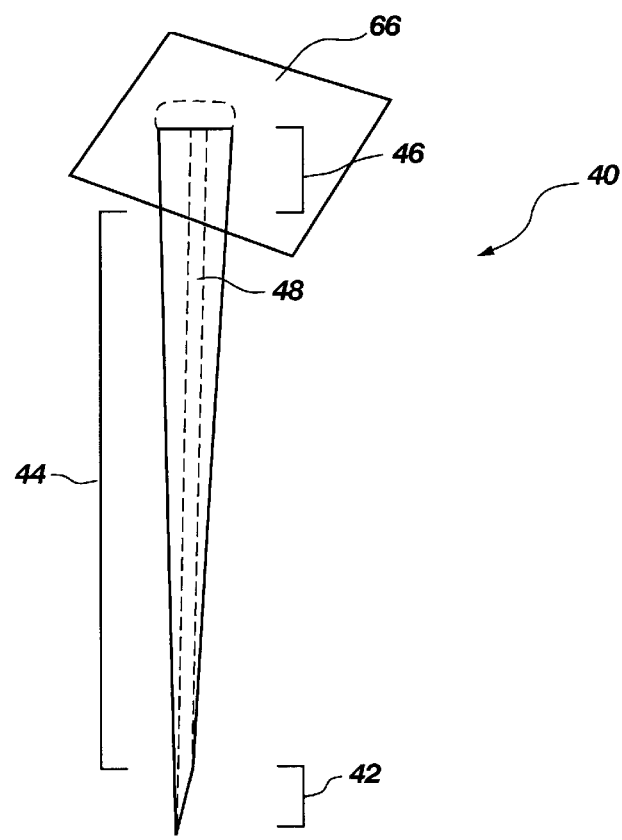
FIG. 5 is a cross-sectional representation of a further embodiment of the electroactive needle shown in FIG. 4.

Electroactive needle 40 is preferably designed to be inserted with the use of light or mild manual compression. Prior to insertion, of course, the skin surface will be properly cleaned and otherwise prepared for needle insertion. As shown in FIG. 5, electroactive needle 40 can be further configured with a platform portion 66 preferably formed of the same electrochemically active materials as electroactive needle 40. Alternatively, platform portion 66 may be formed of various other suitably rigid, but not electrochemically active, materials. Platform portion 66 of electroactive needle 40 surrounds shank 46 and the external opening therein to provide a planar supporting surface for the exertion of manual compression leading to the insertion of electroactive needle 40 into skin 60. Platform portion 66 may be coplanar with a top surface of shank 46, or may extend outwardly from a more distal surface portion of shank 46 in parallel or substantially parallel fashion, depending upon the intended angle of insertion of electroactive needle 40, the length and diameter of electroactive needle 40, and the like.

Platform portion 66 thus remains on the exterior of skin surface 60 after the insertion of electroactive needle 40 into skin surface 60. When formed of the same electrochemically active materials as electroactive needle 40, platform portion 66 forms an electrochemically active portion of active electrode 38. Platform portion 66 can also be configured as a basement portion of a housing adapted as an enclosure for electrode 38, reservoir 52, and/or the entire electrotransport apparatus 32.

One of skill in the art will also recognize that platform portion 66 can perform a supportive and/or interconnective function with regard to reservoir 52. It should be further recognized that conductive wires 56 can be attached to platform portion 66 to provide an electrical path between electrodes 38, 50. Platform portion 66 also helps the user insert the electroactive needle 40 to the proper depth beneath the skin. Moreover, platform portion 66 tends to press against the skin at the insertion site of electroactive needle 40, which substantially eliminates or reduces any bleeding which might result from the insertion.

Figure 6:
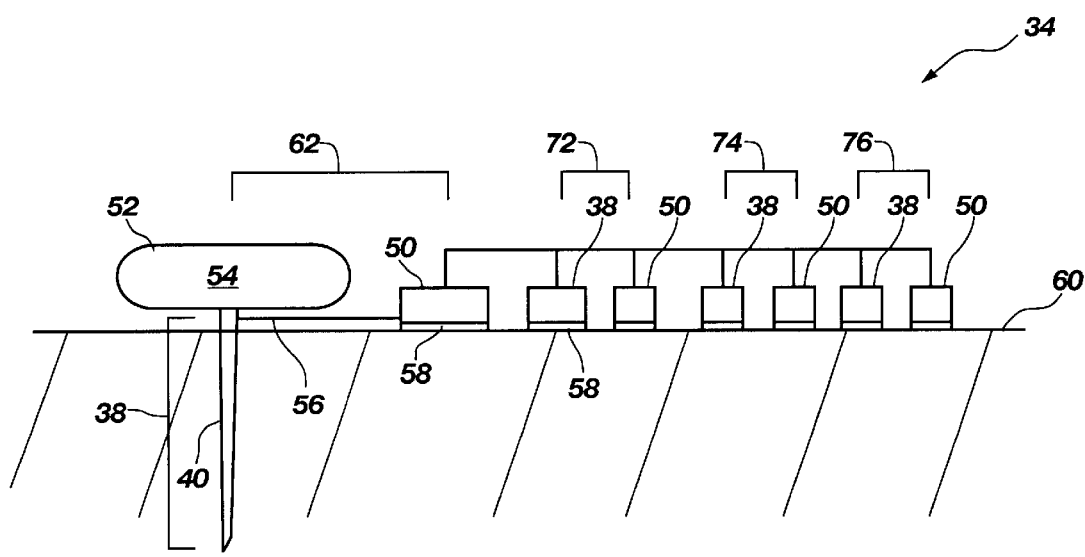
FIG. 6 is a simplified schematic view of a voltage-enhancing embodiment of an electrochemical transdermal delivery system according to the present invention.

To increase and/or to sustain the level of voltage at electroactive needle 40, a plurality of electrochemically active cells 62, 72, 74, 76, etc., may be provided and connected in series for higher voltage across the skin 60, as shown in electrotransport system 34 (FIG. 6). By "connected in series" it is meant that an anode electrode 38 of one or more electrochemical cells 62, 72, 74, 76 is electrically connected to a cathode electrode 50 of one or more other electrochemical cells 62, 72, 74, 76 such that the electrochemical cells 62, 72, 74, 76 are connected to one another by positive terminal (anode) to negative terminal (cathode), or vice versa. In this arrangement, the voltage generated is drawn from an electrochemical cell (e.g., an electrically interconnected anode electrode 38 and cathode electrode 50) at the end of the series string. Electrochemical cells 62, 72, 74, 76 connected in series supply the same current, but produce a higher voltage. A conductive adhesive 58 may be provided under each electrode 38, 50 on a skin surface 60 to stabilize the electrodes 38, 50.

The multiplied voltage resulting from the series of additional electrochemical cells 62, 72, 74, 76, etc., is ultimately relayed to electroactive needle 40 and receiving electrode 50 of electrochemical cell 62, wherein the increased resultant voltage can be delivered through the deeper layers of the skin, the tissues, and/or the systemic circulation. The increase in transport voltage will be proportional to the enhancement of delivery of the beneficial fluids. Varying numbers of cathodes and anodes may be arranged in series to produce a desired voltage, thus more readily facilitating the delivery of high molecular weight drugs or agents, and providing for controlled and tailored delivery of various concentrations of medicaments in beneficial fluids. The electromotive force of the cell may further be enhanced by the choice of metals, composites and the like for the electrodes wherein the anode material and the cathode material are selected from materials having maximum difference in potentials according to the electromotive series.

The invention as described herein above has involved an electrochemical cell wherein voltages, driving forces and successful operation are derived from the device acting as a galvanic cell.

Figure 7:
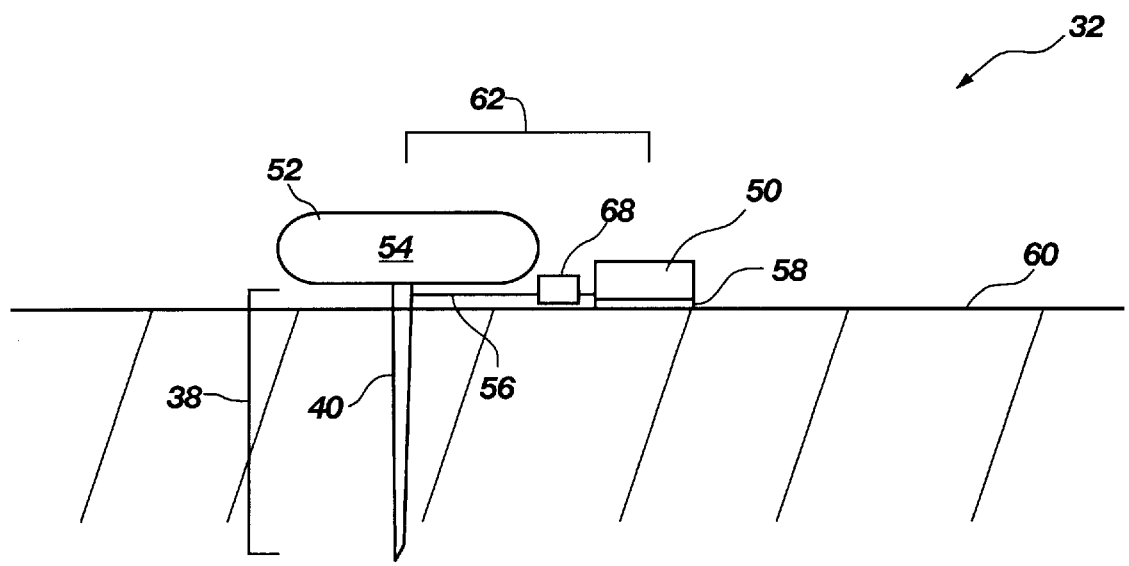
FIG. 7 is a schematic view of another voltage-enhancing embodiment of the electrochemical transdermal delivery system according to the present invention.

In another preferred embodiment shown in FIG. 7, electrotransport system 32 further includes a power source 68 (typically a battery or power cell) interposed between electrodes 38, 50 to assist electrochemical cell 50 by delivering additional direct current to electrodes 38, 50 via conductive wires 56. Similar to the situation of electrochemical cells 62, 72, 74, 76 shown in FIG. 6, power source 68 acts to increase the voltage delivered at electroactive needle 40 while supplying the same current. The increased transport voltage allows for increases in the electrotransport of the drugs or other beneficial agents in beneficial fluids 54. Since a certain level of voltage is electrochemically generated by electrodes 38, 50, and because electroactive needle 40 penetrates the resistive barrier of the stratum corneum, the size and profile of the power source (e.g., battery) 68 can be greatly reduced, resulting in smaller over-all size of the electrotransport system of the present invention in comparison to conventional iontophoretic systems. In a battery-assisted system, the materials selected for the anode and cathode may be different than for purely galvanic cells, since less internal generation of electromotive force is required.

One of skill in the art will recognize that a resistor (not shown) may be interposed in the forward electron flow path of conductive wires 56, as opposed to the return path, to control the flow of current from power source 68. The collective arrangement of resistor and power source 68 thus forms a "voltage controller," as may be referred to hereinafter.

Figure 8:
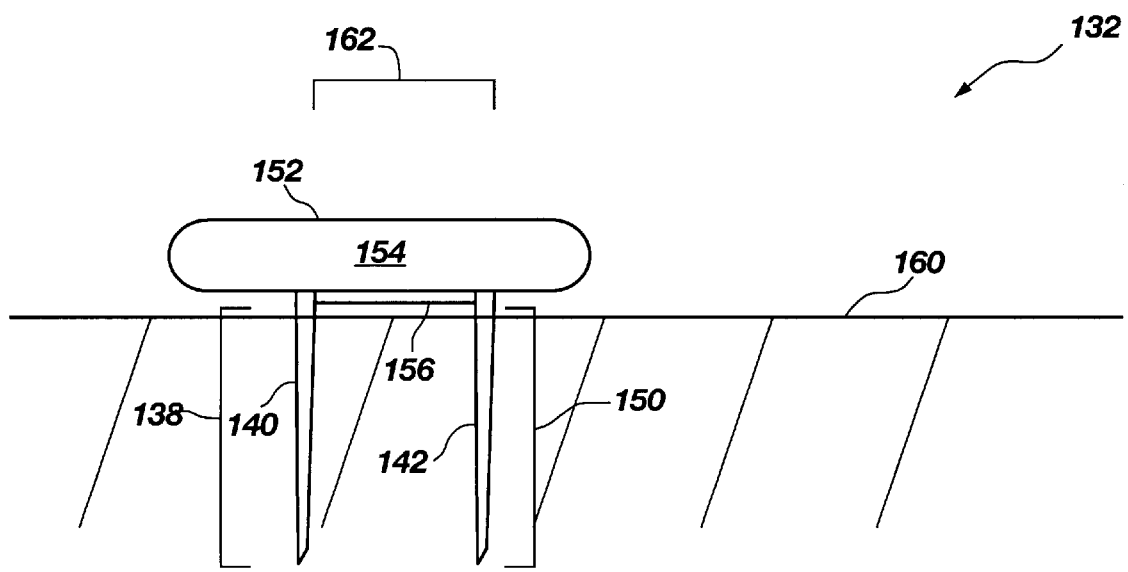
FIG. 8 is a schematic view of another preferred embodiment of an electrochemical transdermal delivery system according to the present invention.

In FIG. 8, an electrotransport system 132 of the present invention is shown configured with two or more electroactive needles 140, 142 as cathodes and anodes 138, 150, respectively, of an electrochemical cell 162. In this embodiment, electroactive needles 140, 142 are formed and configured as described in relation to FIGS. 2, 3, 4 and/or FIG. 5, wherein one or both electroactive needles 140, 142 of cathode and anode 138, 150 include a hollow bore passageway extending through shank, shaft and tip portions of the needles for transdermal delivery of beneficial fluids 154 contained within reservoir 152. A conductive wire 156 extending between electroactive active needles 140, 142 of cathode and anode 138, 150 electrically interconnects electroactive active needles 140, 142, thus establishing electrochemical cell 162.

Reservoir 152 is in fluid communication with one or both of electroactive needles 140, 142 of cathode and anode 138, 150 such that delivery of beneficial fluids 154 can be effected through one or both of electroactive needles 140, 142. Electrotransport system 132 is activated upon insertion of each of electroactive needles 140, 142 into the skin 160, wherein the transdermal delivery of beneficial fluids 154 is facilitated by the electron path resulting from the varying electromotive potentials of electroactive needles 140, 142. Since each of electroactive needles 140, 142 is inserted some, most, or all the way through the stratum corneum of skin 160, significant reductions in the innate resistance of the skin 160 result. Thus, the level of voltage required to be electrochemically generated by electroactive needles 140, 142 for facilitated transport of beneficial fluids 154 is minimal. As in the embodiments described in relation to FIGS. 6 and 7, the voltage produced by electrotransport system 132 can be increased by the inclusion of additional electrochemical cells arranged in series or by the introduction of an assisting additional power source, such as a battery.

One advantage of the use of multiple needles is that larger quantities of beneficial fluids can be delivered over a shorter period of time. Other advantages include larger diffusion areas for drug (beneficial fluid) delivery, increased material for longer lasting cathode or anode performance, and minimization of skin damage caused by the width of any one particular electroactive needle shaft.

Figure 9:
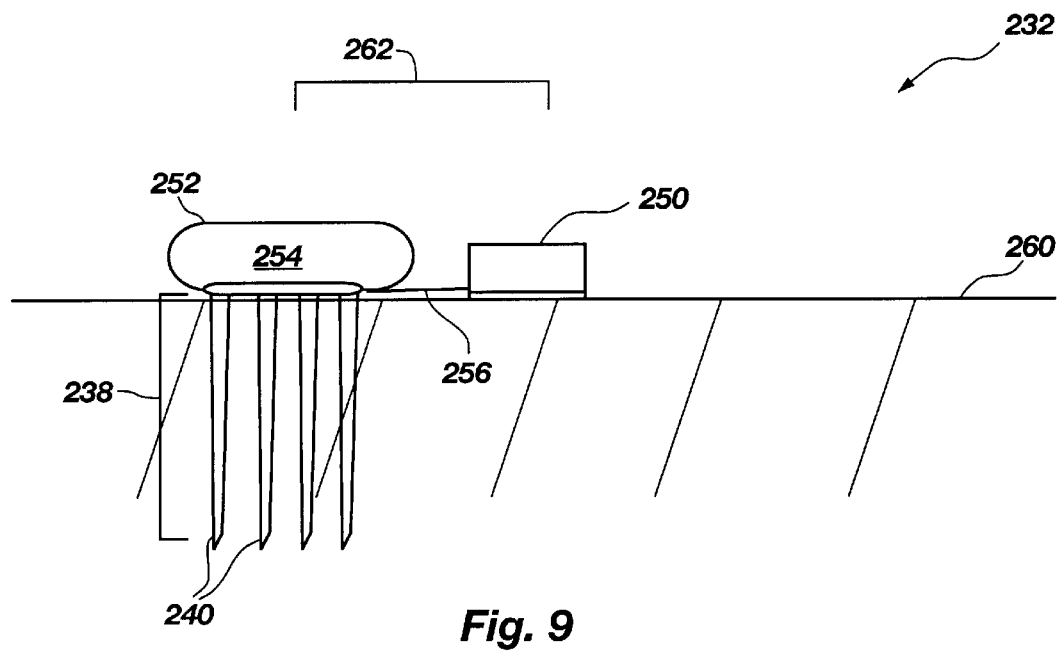
FIG. 9 is schematic representation of a preferred embodiment of an electrode according to the present invention.

FIG. 9 represents another preferred embodiment of an electrotransport system 232, wherein at least one electrode of electrodes 238, 250 of an electrochemical cell 262 is comprised of a plurality of electroactive needles 240. A conductive wire 256 provides an electrical path between, active electrode 238 (comprising electroactive needles 240), and a receiving electrode 250 of a varying electromotive potential, thus establishing electrochemical cell 262. Receiving electrode 250 is constructed and configured-as previously described with regard to FIG. 2.

Electroactive needles 240 together comprise a single active electrode 238, and are thus electrically interconnected by integral construction, conductive bridges, and the like. Accordingly, each of electroactive needles 240 is formed of like materials suitable for the respective use of electrode 238 as a cathode or anode (as previously described with regard to FIG. 2). In terms of design and function, each of electroactive needles 240 is constructed consistently with one or more of the embodiments described in FIGS. 2, 3, and 4. Electroactive needles 240 are thus each configured for the electrically assisted transdermal, intradermal and/or subcutaneous delivery of beneficial fluids 254.

A reservoir 252 containing beneficial fluids 254 interfaces with each of electroactive needles 240 such that beneficial fluids 254 are in fluid communication with the interior passageways with each electroactive needle 240. Electrotransport system 232 is activated upon the insertion of electroactive needles 240 into the skin 260 in conjunction with placement of electrode 250 on a spaced apart skin surface. Insertion of electroactive needles 240 takes place by manual compression. Preferably, electroactive needles 240 are distributed spatially along on a flexible material, such tape or a pliable resin, to allow electroactive needles 240 to be pressed into skin 260 sequentially, or in small groups, such that the ratio of force (i.e., compression) per unit area of skin is maximized. Various patterns and spatial arrangements of electroactive needles 240 are contemplated, however, dependent upon the particular therapeutic application. Upon activation of electrotransport system 232, electrochemical cell 262 generates a current which is applied under skin 260 by the plurality of electroactive needles 240. The electrochemically-generated current then facilitates the transdermal, intradermal and/or subcutaneous transport of beneficial fluids 254 from electroactive needles 240 into the underlying and/or surrounding tissues of the patient's body. One of skill in the art will recognize that an additional power source (e.g., a battery) or additional electrochemical cells arranged in series, may be easily incorporated into electrotransport system 232 to increase the system voltage. Where an additional power source has been incorporated into electrotransport system 232, a resistor is preferably included in the circuit to control the voltage flow toward electrode 238.

Figure 10:
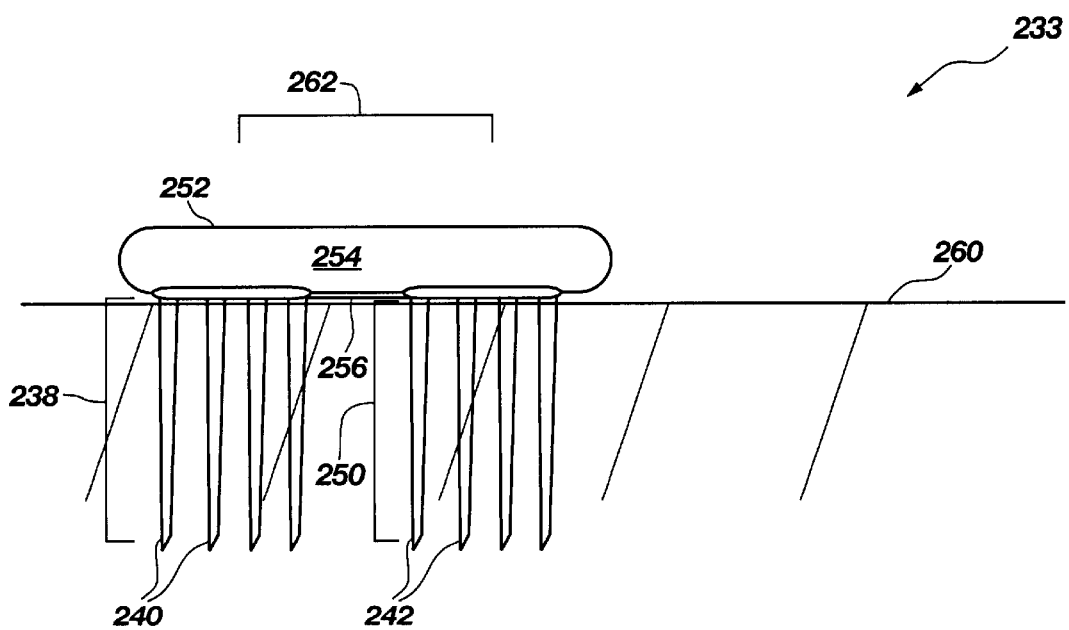
FIG. 10 illustrates a variation of the preferred electrode embodiment of FIG. 9 according to the present invention.

One of skill in the art will further recognize that receiving electrode 250 may also be constructed as a plurality of electroactive needles 242, as well as interfaced with reservoir 252 for delivery of beneficial fluids 254, as is shown in electrotransport system 233 depicted in FIG. 10.

Figure 11:
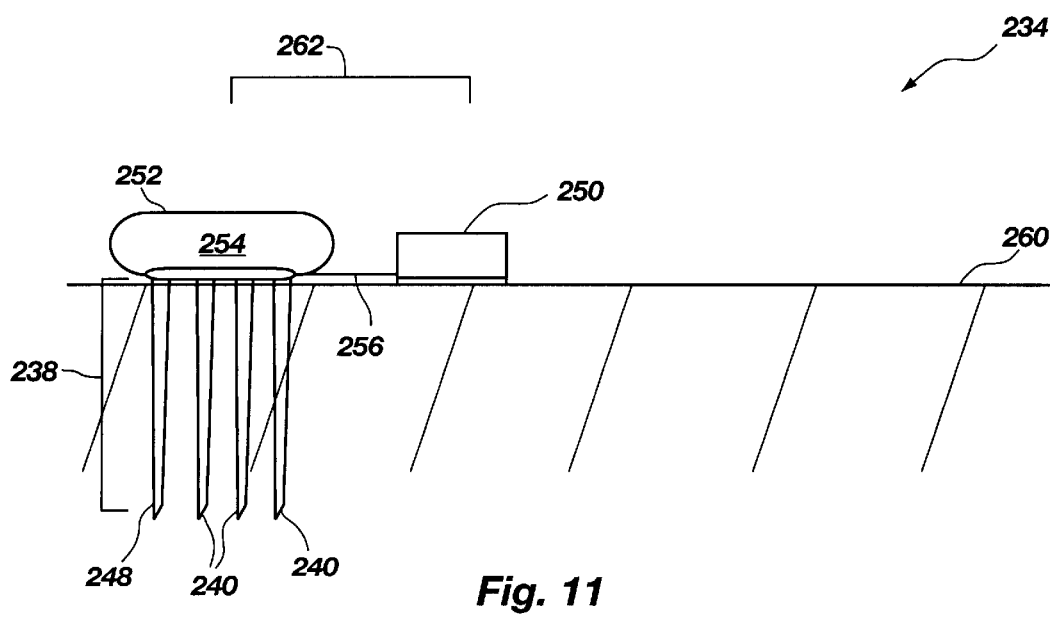
FIG. 11 illustrates a further variation of the preferred electrode embodiment of FIG. 9 according to the present invention.

A variation of the embodiment shown in FIG. 9 is illustrated in electrotransport system 234 (FIG. 11). In this aspect of the present invention, some of the electroactive needles comprising electrode 238 have been formed so as to be of solid construction, rather than as having hollow passageways as described in relation to FIG. 9. Preferably, the solidly formed electroactive needles 248 are positioned peripherally in relation to electroactive needles 240 formed with hollow passageways therethrough. Thus, while each of electroactive needles 248 and 240 is configured to be electrochemically active and to distribute current into the skin 260 of a patient, only electroactive needles 240 formed with hollow passageways are in fluid communication with beneficial fluids 254 within reservoir 252. The delivery of current from solidly formed electroactive needles 248 electrically assists the transport of beneficial fluids 254 as delivered from electroactive needles 240. Solidly formed electroactive needles 248 add electrochemically active material to electrode 238, and increase the delivery area of electrical current flowing from electrode 238. Thus, solidly formed electroactive needles 248 increase the voltage-generating life span of electrode 238, and additionally allow for modifications in the electrically assisted migration pattern of beneficial fluids 254. As an alternative embodiment, a skin-piercing microparticle known in the art may be substituted for one or more solidly formed electroactive needles 248.

Figure 12:
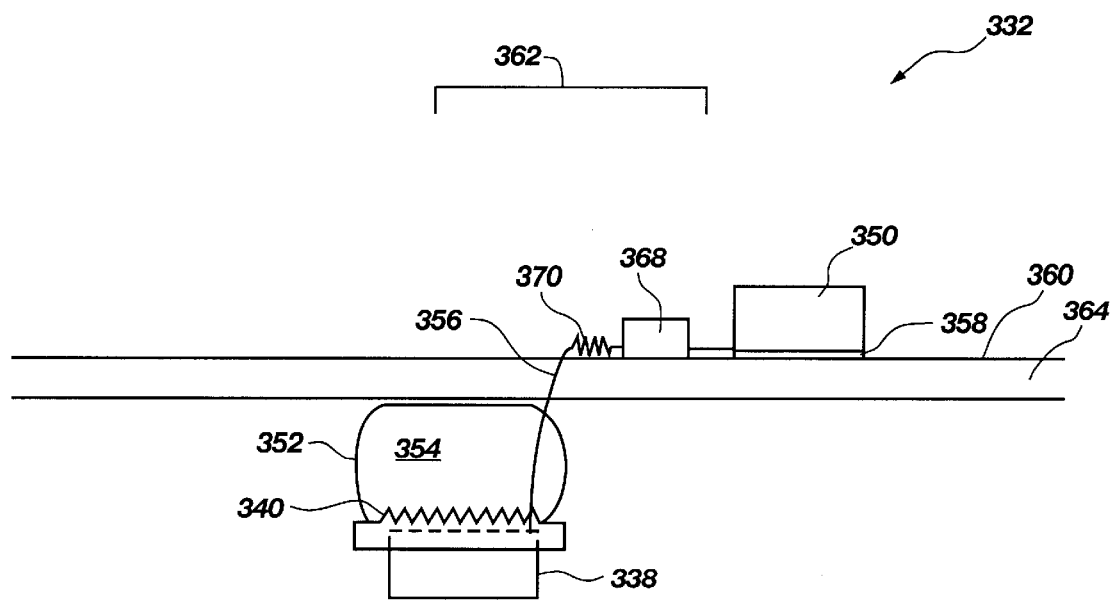
FIG. 12 illustrates an implantable embodiment of the present invention.

FIG. 12 illustrates an embodiment of an implantable electrotransport system 332. In this embodiment, one of an anode and cathode electrode 338, 350 is surgically implanted under a skin surface 360 of a subject, preferably to a depth just exceeding that of the stratum corneum 364. One of skill in the art will recognize that lesser or greater implantation depths may be used dependent upon the particular beneficial application. Preferably, electrodes 338, 350 are electrochemically active and are of differing electromotive potentials so as to form an electrochemical cell 362. Representative materials for the composition of both electrodes 338, 350 have been previously described in relation to the electrotransport system of FIG. 2. Most preferably, electrode 338 is configured as an anode ("anode 338").

As shown in FIG. 12, anode 338 is implanted while cathode 350 remains extracorporeally on skin surface 360.

An insulated connecting wire 356, extending through the skin surface 360 to anode 338 and cathode 350, electrically interconnects electrodes 338, 350. Placement of cathode 350 on skin surface 360 (preferably stabilized with a conductive adhesive 358), along with the electrical interconnection provided by connecting wire 356, creates an electrical circuit and activates electrotransport system 332. The activation of electrotransport system 332 results in electrochemical generation of power (voltage) by electrochemical cell 362 that is capable of facilitating the diffusion of fluids through the tissues of a subject, the fluids and voltage delivered by way of anode 338. An additional power source 368 (typically a battery) is preferably added to the circuit in furtherance of increased and/or sustained voltage. In the event that a power source 368 is used, a resistor 370 will preferably be interposed between power source 368 and anode 338 to control the flow of current through anode 338.

Still referring to FIG. 12, a preferred embodiment of an implantable electrotransport system 332 comprises an implanted electrode (in this case, anode 338) wherein the implanted electrode is configured as a porous metal substrate of a predetermined thickness. Preferably, the implanted electrode 338 will be micro-porous throughout and comprise a substrate formed of an active metal oxide configured in a finely interwoven "wool" or "mesh" for reasons to be discussed hereinafter. The implanted electrode 338 may also be formed of other active materials, including halides, sulfides, alloys, and various mixtures of metal oxides, halides, sulfides, and alloys. A reservoir 352, containing beneficial fluids 354 therein, is implanted with anode 338 and in fluid communication therewith. Preferably, anode 338 is configured with a micro-porous external surface and having a rasp-like surface 340, comprising a plurality of sharp, raised, pointed projections, situated thereon. Rasp-like surface 340 may be integral to anode 338 or provided as a separate component which is sealably interfaced with anode 338. When anode 338 is fitted with reservoir 352, rasp-like surface 340 pierces a central bottom portion of reservoir 352 to allow beneficial fluids 354 to flow therefrom. Reservoir 352, rasp-like surface 340 and anode 338 are otherwise interfaced with one another in a sealable arrangement with respect to beneficial fluids 354 in reservoir 352 and the surrounding tissue of a subject. The porous or sieve-like nature of anode 338 is preferably adapted to be substantially uniform throughout anode 338, allowing beneficial fluids 354 to flow, or percolate, into interior portions of anode 338 and to flow, or percolate, out of one or more exterior surfaces of anode 338 in a fairly evenly distributed manner.

Upon beneficial fluids 354 entering the porous anode 338, the porosity of anode 338 will allow beneficial fluids 354 to progress therethrough in a flow-retarded fashion. The flow rate of beneficial fluids 354 will thus vary according to the thickness and porosity of anode 338, the rheology of beneficial fluids 354, and increases in diffusion of beneficial fluids 354 caused by the electrical current applied to adjacent tissue areas by anode 338. One of skill in the art will recognize that delivery flow rates for a particular concentration of drugs or other beneficial agents contained in beneficial fluids 354 can thus be optimized in terms of dosage over time by adjustment of any of these parameters.

Additionally, anode 338 may be configured of a size and shape known in the art (e.g., provided in thin small outline form) which allows anode 338 to remain in an implanted state for an indefinite period of time without interfering with the normal daily activities of the subject, and with little or no discomfort and physiological reaction to the implanted device. Furthermore, it is preferable that anode 338 be coated for the protection and biocompatibility of anode 338, and/or for focused delivery of beneficial fluids 354. Methods and materials suitable for coating anode 338 have been previously described with respect to shaft 44 of electroactive needle 40 (see discussion of FIG. 3). Benefits of electrotransport system 332 with implantable anode 338 include sub-stratum corneum transfer of beneficial fluids 354, as well as a relatively large diffusion area for beneficial fluids 354 owing to the porous fluid delivery surface area of anode 338.

Figure 13:
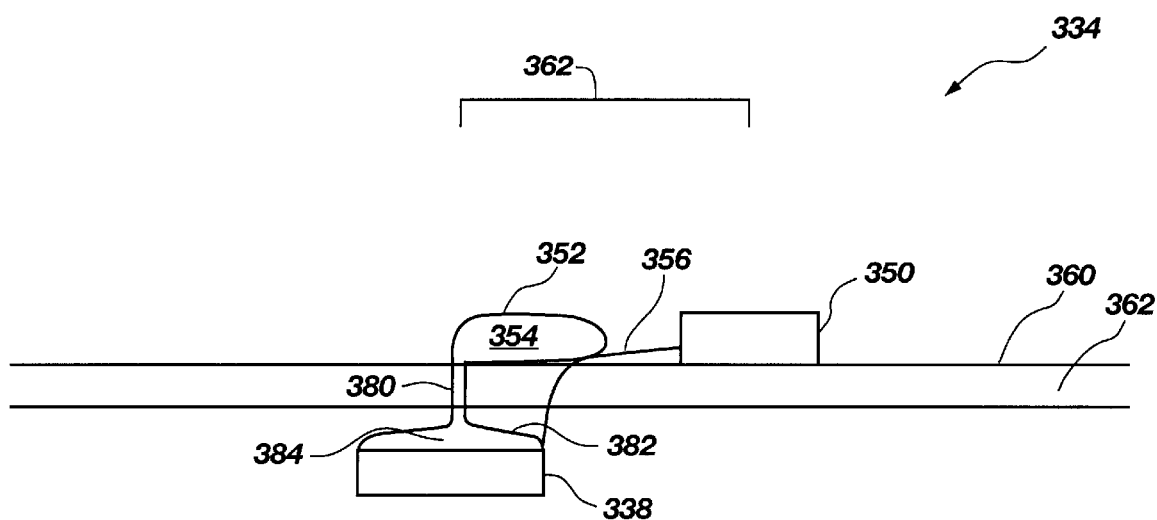
FIG. 13 illustrates a variation of the implantable embodiment of FIG. 12.

FIG. 13 shows an alternate embodiment 334 of the electrotransport system of FIG. 12. In this embodiment, the configuration is similar except that reservoir 352 is placed on a skin surface 360 overlying anode 338, and in fluid communication with porous anode 338 by means of a fluid transport intermediary, shown as a catheter 380, which extends through skin surface 360. Preferably, catheter 380 sealably attaches to reservoir 352 at one end, where catheter 380 and reservoir 352 may be interfaced in a detachable manner. Catheter 380 is sealably attached to a second reservoir 382 of reduced size in relation to reservoir 352, at a second catheter end. Catheter 380 thus allows transfer of beneficial fluids 354 from reservoir 352 to second reservoir 382. In a preferred embodiment, catheter 380 and second reservoir 382 are integrally fashioned as a single component. Reservoir 382 is provided immediately adjacent anode 338, and is thus implanted under a skin surface of a subject along with anode 338. Reservoir 382 is configured to store and deliver beneficial fluids 354 over a porous surface region of anode 338 for percolation therethrough, as previously discussed. This embodiment is additionally advantageous in that the diameter of catheter 380 provides another means for controlling dosage, and that reservoir 352 can be readily exchanged or refilled with additional beneficial fluids 354.

Figure 14:
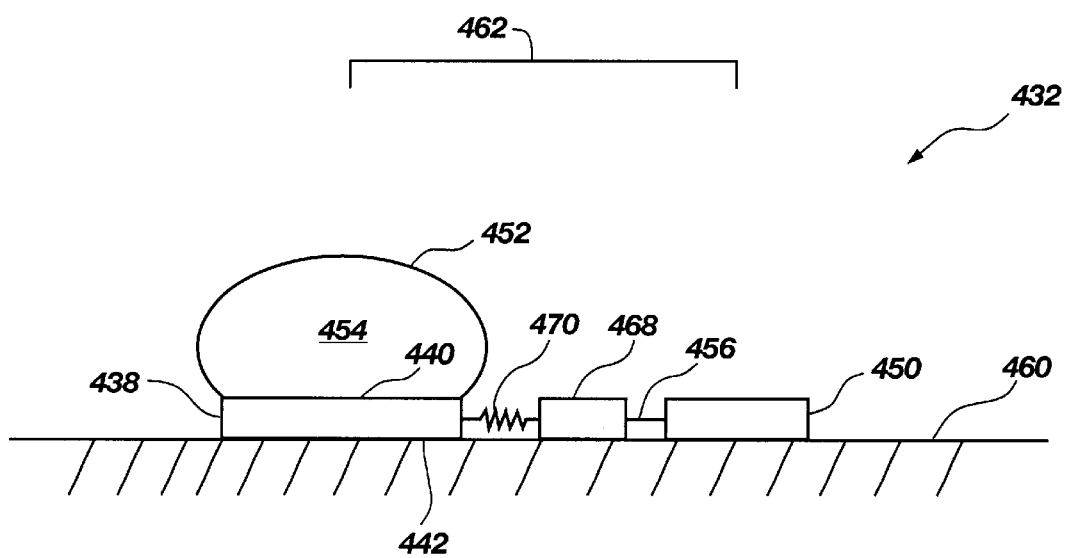
FIG. 14 is a schematic representation of an embodiment of the present invention mounted on a skin surface.

In a still further embodiment shown in FIG. 14, an electrotransport system 432 comprises an electrochemically active porous anode electrode 438, conceptually similar to anode 338 of FIG. 12, placed on the skin surface 460 via a skin contact area 442 of anode 438. An electrochemically active cathode electrode 450 is also provided on skin surface 460 in a spaced-apart relationship with anode 438. Materials for the composition of electrochemically active electrodes 438, 450 have been previously described in relation into the electrotransport systems of FIGS. 2 and 12. A connecting wire 456 electrically interconnects electrodes 438, 450, creating an electrochemical cell 462.

In one aspect of this embodiment, anode 438 may be formed of a porous metal substrate of a predetermined thickness, such as a finely interwoven metal oxide wool or mesh. In an alternate embodiment, anode 438 may be formed of a porous and active metal oxide-filled polymer or adhesive. As one example, a microporous and active metal oxide-filled polymer tape may be used as anode 438. Anode 438 is preferably provided with a relatively thin cross-section in relative to cathode 450. The active metal oxide filler will preferably.comprise materials such as Zn, Mg, Ca, Ba, Sn, Fe, as well as their alloys and mixtures. A conductive adhesive (not shown) may be supplied under anode 438 and/or cathode 450. Preferably, however, the innate material composition provided for the porous and active metal oxide-filled polymer or adhesive, will provide sufficient adherence for anode 438 to be stabilized with respect to skin 460.

A reservoir 452 containing beneficial fluids 454 is provided adjacent a reservoir mounting surface 440 of anode 438 and in fluid communication with pores or micro-pores thereof. Reservoir 452 is otherwise fitted to anode 438 in a sealed and airtight arrangement by methods known in the art. An additional power source 468 (typically a battery) and a resistor 470 are preferably added to the circuit as previously described. Power source 468 will preferably provide sufficient voltage, alone or in combination with the electrochemical generation of power from anode 438 and cathode 450, to establish a "skin breakthrough voltage" which overcomes the resistive properties of the stratum corneum.

Preferably, anode 438 will have uniform porosity throughout, and will be insulatively coated or otherwise sealed on its exterior surfaces, excluding, of course, the fluid transporting regions of reservoir mounting surface 440 and skin contact area 442. As in the case of anode 338 of FIG. 12, the porosity of anode 438 will allow beneficial fluids 454 to advance and percolate, in a flow-retarded fashion from reservoir 452, through anode 438, and out the bottom surface of skin contact area 442. Upon activation of the electrochemical cell 462 by placing anode 438 and cathode 450 on the skin 460, a circuit is created, as previously described, for the delivery of direct current through the skin layers. The direct current produced electrochemically by anode 438 and cathode 450, or the voltage attributable to power source 468, increases the rate of transdermal flux of beneficial fluids 454 by reducing the physical resistance and/or enhancing the permeability of the tissue layers underlying anode 438.

Figure 15:
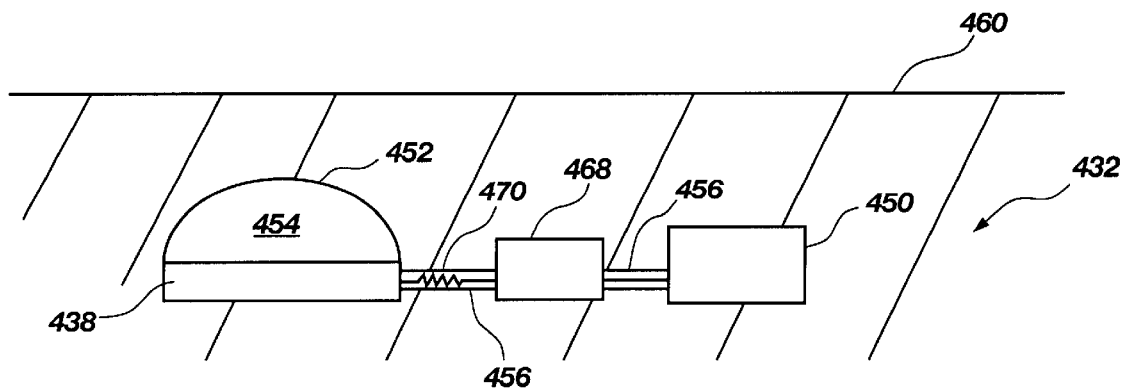
FIG. 15 illustrates an embodiment of the present invention which is entirely implantable under the skin.

In a final embodiment, the entirety of the electrotransport apparatus of FIG. 14 can be adapted to be implanted below a skin surface of a subject, as is illustrated in FIG. 15. Like reference numerals are provided in FIG. 15 for the like components previously shown in FIG. 14. As indicated in the figure, each of anode 438, cathode 450, reservoir 452, insulated connecting wire 456, power source 468, and resistor 470 of electrotransport apparatus 432 may be subcutaneously implanted under a skin surface 460. Preferably, electrotransport apparatus 432 is implanted to a depth which is at least below the depth of the stratum corneum layer of the skin 460. In this embodiment, the transdermal flux of beneficial fluids 454 is enhanced as both anode 438 and cathode 450 may advantageously deliver electrical current without hindrance from the stratum corneum barrier layer.

In this embodiment, anode 438 can be provided as a porous metal substrate of a predetermined thickness, and configured as previously described in relation to implantable electrode 338 of FIG. 12. The reservoir 452 and anode 438 are also preferably interfaced as previously described in relation to FIG. 12. A unitary housing (not shown) made of biocompatible material will preferably be provided over anode 438, cathode 450, reservoir 452, insulated connecting wire 456, power source 468, and resistor 470. The unitary housing may serve to position anode 438 and cathode 450 a predetermined separation distance from one another, as well as function to protect and stabilize electrotransport system 432 during handling, implantation, and while functioning under the skin 460. The unitary housing, which may be molded by processes known in the art for a secure fit over the components of electrotransport system 432, is configured to not interfere with the electrical flow from anode 438 and cathode 450 to the tissues under the skin. The unitary housing will also preferably be configured of a size and shape known in the art (e.g., provided in thin small outline form) which allows electrotransport system 432 to remain in an implanted state for an indefinite period of time without interfering with the normal daily activities of the subject, and with little or no discomfort and physiological reaction to the implanted device.

The above-described apparatus and methods according to the present invention represent an improvement over conventional iontophoretic systems. Since the electroactive needle of the present invention extends all or part way through the stratum corneum of a skin surface, the keratinous and bilipid barriers of the outermost skin layer can be breached, resulting in a substantial reduction in impedance to the voltage electrochemically generated by the apparatus. The electrochemically generated voltage from the electrodes of the system thus facilitates the flow of the beneficial agents into patient tissue which underlies and/or surrounds the electroactive needle without the need for a "skin breakthrough voltage." Additionally, the apparatus and methods according to the present invention bypass potential alterations to the charge of a beneficial substance which may otherwise occur as a result of the relatively low pH on the outer surface of the skin. Thus, the apparatus and methods of the present invention are particularly suited for the delivery of therapeutic proteins and peptides.

It will be appreciated by those skilled in the art that the embodiments herein described, while illustrating certain embodiments, are not intended to so limit the invention or the scope of the appended claims. Those skilled in the art will also understand that various combinations or modifications of the preferred embodiments could be made without departing from the scope of the invention.

Once being apprised of the instant invention, methods of making and using it will become apparent to one of ordinary skill in the art. For example, the apparatus of the present invention can be easily adapted to accept standard medication cartridges (a type of reservoir) which are pre-loaded with fluids comprising drugs and other beneficial agents. The reservoir may also be configured to be interfaced with one or both of the electrodes of the present invention in various orientations. In addition, a semipermeable membrane, preferably permeable to a non-ionic form of the therapeutic agent in the beneficial fluid reservoir, is also contemplated for use in the present invention. The semipermeable membrane could be interposed, for example, between the beneficial fluid reservoir and the shank end of the electroactive needle. Various circuitry elements, such as resistors, transistors and capacitors, can be incorporated into the circuitry of the apparatus, as could a microprocessor and LED to record and display the date, the time, and the amount of each medication (beneficial fluid) administration. Also, the electroactive needles of the present invention can be sterilized between uses by sterilization techniques known in the art. Alternatively, the electroactive needles may be disposed of after a single use.

Additionally, the skin surface may be conditioned with bromelain, papain or similar skin conditioners which remove or alter the stratum corneum whereby electroactive needle penetration may be facilitated, the electrotransport circuit more easily realized, and the flow of delivered fluids more readily be transported along solid needles to a substratum corneum delivery site. Skin-piercing microparticles known in the art could likewise be used in conjunction with the electroactive needles, skin conditioners, and other device embodiments disclosed herein to further reduce the resistive properties of the stratum corneum.

Thus, while certain representative embodiments and details have been shown for purposes of illustrating the invention, it will be apparent to those skilled in the art that various changes in the invention disclosed herein may be made without departing from the scope of the invention, which is defined in the appended claims.

What is claimed is:

1. An electrotransport apparatus for delivery of a drug or other beneficial agent through a body surface of a subject, comprising:

an electrochemical cell having an electrochemically active cathode and an electrochemically active anode;

at least a portion of at least one of the electrochemically active cathode and the electrochemically active anode configured as at least one electroactive needle, wherein the at least one electroactive needle is configured for conducting current in relation to the body surface and for delivering the drug or other beneficial agent across the subject's body surface; and a conductor for electrically interconnecting the electrochemically active cathode with the electrochemically active anode;

wherein said electrochemically active anode and said electrochemically active cathode form a power source for said electrotransport apparatus.

2. The electrotransport apparatus of claim 1, wherein the at least one electroactive needle is configured for the delivery of the drug or other beneficial agent in liquid form.

3. The electrotransport apparatus of claim 2, wherein the at least one electroactive needle is adapted for insertion into a skin surface by manual compression.

4. The electrotransport apparatus of claim 3, wherein the at least one electroactive needle is adapted for one of intravenous and intramuscular delivery of the drug or other beneficial agent.

5. The electrotransport apparatus of claim 1, wherein at least one of the electrochemically active cathode and the electrochemically active anode comprises a plurality of electroactive needles.

6. The electrotransport apparatus of claim 1, wherein at least a portion of each of the electrochemically active cathode and the electrochemically active anode are formed of the at least one electroactive needle.

7. The electrotransport apparatus of claim 1, further comprising a drug or other beneficial agent reservoir attached proximate at least one of the electrochemically active cathode and the electrochemically active anode.

8. The electrotransport apparatus of claim 7, wherein the drug or other beneficial agent reservoir is attached proximate the at least one electroactive needle and in fluid communication therewith.

9. The electrotransport apparatus of claim 8, wherein the drug or other beneficial agent reservoir comprises a standard medication cartridge.

10. The electrotransport apparatus of claim 1, further comprising an additional power source electrically interconnected to the electrochemically active cathode and the electrochemically active anode.

11. The electrotransport apparatus of claim 1, further comprising a second electrochemical cell connected in series with the electrochemical cell.

12. The electrotransport apparatus of claim 1, wherein at least a portion of each of the electrochemically active cathode and the electrochemically active anode are configured as a plurality of electroactive needles.

13. The electrotransport apparatus of claim 1, wherein the electrochemically active anode is formed of an electrochemically active metal, and wherein the electrochemically active cathode is formed of a material selected from the group consisting of electrochemically active oxides, halides, and chalcogenides.

14. The electrotransport apparatus of claim 13, wherein the electrochemically active anode is formed of a metal selected from the group consisting of Zn, Mg, Ca, Ba, Sn, Fe, their alloys, and mixtures of any thereof.

15. The electrotransport apparatus of claim 13, wherein the electrochemically active cathode is formed of a material selected from the group consisting of carbon, active metal oxides, and mixtures and composites of any thereof.

16. The electrotransport apparatus of claim 13, wherein the active metal oxides are selected from the group comprising silver oxides, copper oxides, manganese dioxides, and mixtures and composites of any thereof.

17. The electrotransport apparatus of claim 1, further comprising a controller configured to regulate voltage passing between the electrochemically active cathode and the electrochemically active anode.

18. The electrotransport apparatus of claim 17, wherein the controller comprises a battery and a resistor interposed in an electrical interconnection extending between the electrochemically active cathode and the electrochemically active anode.

19. The electrotransport apparatus of claim 1, wherein the at least one electroactive needle is associated with a compound having anti-microbial activity.

20. The electrotransport apparatus of claim 1, wherein at least a portion of the at least one electroactive needle is coated with a polymer.

21. An improved transdermal delivery apparatus of the type in which an electrochemically active anode is configured to conduct current in relation to a first skin surface, an electrochemically active cathode is configured to provide an electric current in relation to a second skin surface, a conductor for electrically interconnecting the electrochemically active anode with the electrochemically active cathode, and in which a reservoir containing a drug or beneficial agent is attached adjacent at least one of the electrochemically active anode and the electrochemically active cathode, wherein the improvement comprises:

at least a portion of at least one of the electrochemically active anode and the electrochemically active cathode configured as at least one electroactive needle configured and adapted to penetrate at least a portion of a stratum corneum layer of a subject; wherein said electrochemically active anode and said electrochemically active cathode form a power source for said transdermal delivery apparatus.

22. The improved transdermal delivery apparatus of claim 21, wherein the at least one electroactive needle is configured for conducting current in relation to a body surface of the subject and for delivering the drug or other beneficial agent through the body surface of the subject.

23. A method of electrically facilitating the transport of a drug or other beneficial agent through body tissues of a subject, comprising:

providing an anode configured to conduct current in relation to a first skin surface;

providing a cathode configured to conduct current in relation to a second skin surface, at least a portion of at least one of said cathode and said anode being configured as at least one electroactive needle of a predetermined length sufficient to penetrate at least a portion of a stratum corneum layer of the subject;

providing at least one conductor for electrically interconnecting said anode with said cathode, said at least one conductor extending between said anode and said cathode;

providing a drug or other beneficial agent reservoir disposed adjacent and in fluid communication with an electrically conducting area of at least one of said anode and said cathode;

inserting said electroactive needle a predetermined distance into a skin surface to electrochemically activate said anode and said cathode;

electrochemically generating a voltage from said activation of said anode and said cathode; and delivering said voltage to body tissues of the subject, said voltage facilitating the transport of the drug or other beneficial agent through said body tissues of the subject; wherein said anode and said cathode form a power source for facilitating the transport of the drug or other beneficial agent.

24. The method according to claim 23, wherein said delivering said voltage to body tissues of the subject comprises conducting said voltage through said at least one electroactive needle.

25. The method according to claim 23, further comprising transporting the drug or other beneficial agent to the body tissues of the subject through a passageway in said electroactive needle.

26. The method of claim 25, wherein said transporting the drug or other beneficial agent comprises transporting the drug or other beneficial agent in liquid form.

27. The method of claim 26, wherein inserting the at least one electroactive needle comprises inserting the at least one electroactive needle into said skin surface by manual compression.

28. The method of claim 23, further comprising lessening electrically resistive barriers of a portion of the stratum corneum by subjecting the portion of the stratum corneum to micro-piercing by microparticles.

29. In a method of fabricating an electrotransport assembly for facilitating the transport of a drug or other beneficial agent through a skin surface, of the type wherein an electrochemically active anode is configured to conduct current in relation to a first skin surface, an electrochemically active cathode is configured to provide an electric current in relation to a second skin surface, an electrical interconnection between the electrochemically active cathode and the electrochemically active cathode, and in which a reservoir containing a drug or beneficial agent is attached adjacent and in fluid communication with at least one of the electrochemically active anode and the electrochemically active cathode, the improvement comprising:

configuring at least a portion of at least one of the electrochemically active anode and the electrochemically active cathode as an electroactive needle for penetrating at least a portion of a stratum corneum layer of a subject; wherein said electrochemically active anode and said electrochemically active cathode form a power source for said electrotransport assembly.

30. The electrotransport apparatus of claim 1, wherein the electrochemical cell consists essentially of the electrochemically active cathode and the electrochemically active anode.

* * * * *

UNITED STATES PATENT AND TRADEMARK OFFICE
CERTIFICATE OF CORRECTION

PATENT NO. : 6,591,133 B1
DATED : July 8, 2003
INVENTOR(S) : Ashok V. Joshi

It is certified that error appears in the above-identified patent and that said Letters Patent is hereby corrected as shown below:

<u>Title page,</u>
Item [56], OTHER PUBLICATIONS, change "date" to -- dated --

<u>Drawings,</u>
FIGURE 13, change the right-most occurrence of "362" to -- 364 --
FIGURE 15, extend the lead lines of "470" and "456" to better indicate the position of the resistor and the wire, respectively.

<u>Column 2,</u>
Line 54, change "added-to" to -- added to --

<u>Column 4,</u>
Line 53, after "to" to -- a --
Line 67, before "other" insert -- or --

<u>Column 7,</u>
Line 38, at the end of the line, after "shank" insert -- end --
Line 50, delete the comma after "the"

<u>Column 9,</u>
Line 25, after "shank" and before "46" insert -- end --

<u>Column 11,</u>
Line 4, before "needles" delete "active"
Line 38, delete the comma after "between"
Line 42, change "configured-as" to -- configured as --
Line 66, at the end of the line, after "such" insert -- as --

UNITED STATES PATENT AND TRADEMARK OFFICE
CERTIFICATE OF CORRECTION

PATENT NO.    : 6,591,133 B1
DATED         : July 8, 2003
INVENTOR(S)   : Ashok V. Joshi It is certified that error appears in the above-identified patent and that said Letters Patent is hereby corrected as shown below:

<u>Column 14,</u>
Line 30, change "354" to -- 384 --
Line 57, change "preferably.comprise" to -- preferably comprise --

<u>Column 15,</u>
Lines 34 and 36, change "apparatus" to -- system --

Signed and Sealed this

Twenty-third Day of December, 2003

JAMES E. ROGAN
*Director of the United States Patent and Trademark Office*